US012562270B2

(12) United States Patent
Grundmann et al.

(10) Patent No.: US 12,562,270 B2
(45) Date of Patent: Feb. 24, 2026

(54) MEDICAL INSUFFLATOR WITH AUTOMATIC PREADJUSTMENT OF OPERATING PARAMETERS

(71) Applicant: W.O.M. WORLD OF MEDICINE GMBH, Berlin (DE)

(72) Inventors: Julia Grundmann, Berlin (DE); Yves Köth, Berlin (DE); Matthias Hildebrand, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 166 days.

(21) Appl. No.: 18/290,500

(22) PCT Filed: May 15, 2022

(86) PCT No.: PCT/IB2022/054512
§ 371 (c)(1),
(2) Date: May 15, 2024

(87) PCT Pub. No.: WO2022/243830
PCT Pub. Date: Nov. 24, 2022

(65) Prior Publication Data
US 2025/0273329 A1 Aug. 28, 2025

(30) Foreign Application Priority Data
May 17, 2021 (DE) ..................... 10 2021 002 546.6

(51) Int. Cl.
| | |
|---|---|
| *G16H 40/63* | (2018.01) |
| *A61M 13/00* | (2006.01) |
| *G16H 10/60* | (2018.01) |
| *H04L 9/40* | (2022.01) |

(52) U.S. Cl.
CPC ............ *G16H 40/63* (2018.01); *A61M 13/00* (2013.01); *G16H 10/60* (2018.01); *H04L 63/0428* (2013.01)

(58) Field of Classification Search
CPC ....... G16H 40/63; G16H 10/60; A61M 13/00; H04L 63/0428
See application file for complete search history.

(56) References Cited

U.S. PATENT DOCUMENTS

| | | | |
|---|---|---|---|
| 2002/0038392 A1* | 3/2002 | De La Huerga ....... | G16H 20/17 710/8 |
| 2008/0294090 A1 | 11/2008 | Heath | |
| 2015/0290387 A1* | 10/2015 | Möllstam ............ | A61M 13/003 604/24 |
| 2015/0332196 A1* | 11/2015 | Stiller .................... | G16H 20/40 705/2 |
| 2016/0196400 A1* | 7/2016 | Hanning ............. | G06F 9/44505 713/100 |
| 2017/0049964 A1* | 2/2017 | Varsavsky .............. | G16H 40/40 |
| 2020/0168313 A1* | 5/2020 | Westerhoff ............. | G16H 70/20 |
| 2020/0168326 A1* | 5/2020 | Westerhoff ............. | A61B 1/015 |
| 2022/0183915 A1* | 6/2022 | Augustine ............. | A61B 5/725 |

FOREIGN PATENT DOCUMENTS

| | | | | |
|---|---|---|---|---|
| DE | 202019005316 U1 | 3/2020 | | |
| EP | 1779887 A2 | 5/2007 | | |
| EP | 3486915 A1 | 5/2019 | | |
| WO | 2016024253 A1 | 2/2016 | | |
| WO | WO-2019020136 A1 * | 1/2019 | ............. | A61B 1/317 |

OTHER PUBLICATIONS

M. Venkatesan and B. Jolad, "Nanorobots in cancer treatment," INTERACT-2010, Chennai, India, 2010, pp. 258-264, doi: 10.1109/INTERACT.2010.5706154. (Year: 2010).*

A. Benkmann et al., "Concept of iterative optimization of minimally invasive surgery," 2017 22nd International Conference on Methods and Models in Automation and Robotics (MMAR), Miedzyzdroje, Poland, 2017, pp. 443-446, doi: 10.1109/MMAR.2017.8046868. (Year: 2017).*

D. Arney, R. Jetley, P. Jones, I. Lee and O. Sokolsky, "Formal Methods Based Development of a PCA Infusion Pump Reference Model: Generic Infusion Pump (GIP) Project," 2007 Joint Workshop on High Confidence Medical Devices, Software, and Systems and Medical Device Plug-and-Play Interoperability (Year: 2007).*

* cited by examiner

*Primary Examiner* — Sun M Li
(74) *Attorney, Agent, or Firm* — Kaplan Breyer Schwarz LLP

(57) ABSTRACT

The invention relates to a device for using individual data from networked medical devices for a simple and safe patient-specific equipment setting of an insufflator.

16 Claims, No Drawings

MEDICAL INSUFFLATOR WITH AUTOMATIC PREADJUSTMENT OF OPERATING PARAMETERS

FIELD OF APPLICATION OF THE INVENTION

The invention relates to a device for using individual data from networked medical devices for a simple and safe patient-specific equipment setting of an insufflator.

"Networking" refers to the comprehensive use of information from all relevant data available in the operating room. The term "medical device" refers to any powered or non-powered technical equipment used for diagnostic or therapeutic interaction with the human or animal body. Accessories and consumables (disposables) are also explicitly referred to as medical devices.

BACKGROUND OF THE INVENTION

WO 2019/020136 A1 and WO 2019/020137 A1 disclose medical devices, which are intended (inter alia) for collecting and analyzing data in the medical device according to the present claims by transferring data from the intraoperative phase and recording new data in the postoperative phase. The publications WO 2019/020136 A1 and WO 2019/020137 A1 also cite other prior art.

A medical system that automatically preadjusts the treatment parameters of an upcoming treatment procedure on a medical device, in particular on an insufflator, from existing data is not yet known.

SUMMARY OF THE INVENTION

According to the invention, a medical system is proposed which automatically preadjusts the treatment parameters of an upcoming treatment procedure on a medical device, in particular on an insufflator, from existing data on the patient and the procedure.

The invention therefore relates to a medical device for insufflation that takes into account already collected individual medical data, comprising (a) at least one interface for reading patient information, in particular to at least one hospital information system (HIS) containing the patient record with the relevant patient data. The interface can be realized, for example, via LAN, WLAN, Bluetooth, etc., and/or an image recognition system for reading patient information (e.g., from a QR code). The patient information required for the current purpose includes at least name, patient ID, age, gender, height, weight, or BMI. Optionally, a photograph of the patient may be included for ease of identification, (b) at least one interface for reading procedure information for the respective patient (type and body site of the intervention, type of diagnostics/therapy) from the hospital information system (e.g. via LAN, WLAN, Bluetooth, etc.), (c) at least one memory unit for storing patient data and procedure data received via the interface, (d) at least one memory unit for storing the possible operating parameters of each connected insufflator (e.g., maximum achievable flow, maximum achievable pressure). Optionally, the possible operating parameters of each available accessory (e.g., tubing set) may be stored (e.g., maximum allowable pressure, humidification option, maximum amount of humidifier), (e) at least one memory unit for storing the allowable operating parameters of an insufflator for different patients (e.g. maximum internal body pressures for patients of different ages, different heights, different BMIs, depending on the treatment procedure), (f) at least one computing unit for determining the operating parameters for the selected treatment procedure for the respective patient, (g) at least one interface to the selected insufflator, the interface transmitting patient data and operating parameters to the memory unit of the insufflator (e.g., via LAN, WLAN, Bluetooth, etc.), (h) optionally at least one interface from the insufflator to the hospital information system for transferring the intraoperative measured data and storing it in the patient record.

The above components (a) to (h) can be integrated into the insufflator or implemented separately. For example, the components can be integral parts of a hospital information system (HIS) (e.g. hospital or OR server), which transfers the determined operating parameters to the insufflator via the interface (g) and the intraoperative data back to the patient record.

DETAILED DESCRIPTION OF THE INVENTION

A preferred embodiment is an insufflator having all components (a) to (h).

The system according to the invention is used as follows:

Following a medical diagnosis, the first step is to propose a treatment, e.g., a specific endoscopic procedure. The surgical planning team must first determine the operating room for such an intervention (hereinafter also referred to as the procedure). Typically, this will also determine the equipment that will remain in the respective operating rooms.

Once the type and location of the procedure and the medical device (or devices) for a particular patient have been determined, the adjustment of the devices with the necessary parameters can begin. To do this, the contents of the patient record are loaded into the system's memory, along with the necessary data about the patient and the procedure:

The relevant patient information includes: name, patient ID, age, gender, height, weight (BMI). Name and patient ID are used to uniquely identify the patient. Age, gender, height, weight (BMI) are used to determine the parameter limits (e.g. maximum internal body pressure). The parameter limits for a patient depend on the surgical site: for example, the abdomen requires and allows a higher pressure than the urinary bladder or the uterus. At the same time, a higher volume is required for the abdomen than for the bladder or uterus.

Relevant procedure data includes: type of diagnosis (ICD code), type of procedure (HCPCS code), expected duration of procedure, instruments required.

The necessary insufflation parameters of the medical device (or devices) can be determined from the patient and procedure data.

These include: minimum pressure inside the body ($p_{min}$), maximum pressure inside the body ($p_{max}$), minimum flow in the inlet ($F_{min,in}$), maximum flow in the inlet ($F_{max,in}$), minimum suction power ($F_{max,out}$), maximum suction power ($F_{max,out}$), need for humidification of the insufflation gas, amount of humidifier, type of instruments required (e.g., shaver, morcellator, RF surgical devices, trocars, and optics), type of tubing sets and other consumables required.

In practice, the insufflation parameters minimum flow in the inlet ($F_{min,in}$) and minimum suction power ($F_{max,out}$) are often 0 L/min.

The parameters can be determined either in the insufflator (centralized) or in a separate microcomputer (decentralized). The latter may be, for example, a surgical server that transmits the determined parameters to the insufflator (e.g., via LAN, WLAN, Bluetooth, etc.). As part of this determination, it can also be checked whether the existing equipment is suitable for the procedure.

A plausibility check is performed immediately prior to surgery: The patient record is scanned electronically (e.g., via a barcode or QR code) and compared with the patient in the operating room. If the data (name, picture, gender, age, height, weight/BMI) matches, the OR personnel can confirm the identity. The determined insufflation data is transmitted to the insufflator. The insufflator checks the connected consumables (especially the tubing set) for compliance with the selected procedure. This test can be used, for example, to check whether a tubing set is connected with or without humidification material. The basis for this check is an information carrier on the tubing set that includes the necessary information. This information carrier can be in the form of a barcode, QR code, or RFID chip. Such tubing sets with information carriers and the associated reading devices and methods are described in the prior art (see, e.g., EP 1779887 A2), so that they need not be explained here. If the connected consumables do not match the planned procedure, a warning is displayed and the device is locked. In an optional embodiment of the invention, other surgical instruments are also checked for compatibility with the selected procedure in a similar manner.

The clinician can manually change the preadjusted values. If the changed values are outside the range appropriate for the combination of patient and procedure, a warning is issued and the unit is locked if necessary.

In a further optional variant, the system also allows fully manual adjustment by the treatment personnel and fully manual operation. However, all operating parameters are still monitored during adjustment manual and operation. If the operating parameters deviate from the specified parameter ranges, a warning signal is output on the display.

In addition, an interface to an anesthesia system can optionally be provided, which, for example, transmits forecasts of possible treatment prolongations so that the sedation can be adjusted if necessary.

Optionally, the system also includes a memory unit and an interface for storing the current intraoperative operating parameters in the patient record of the hospital information system (HIS). Storage of images and videos, especially endoscopic images, can also be integrated.

It goes without saying that all data transmissions are preferably encrypted. Transmission and encryption systems and protocols are state of the art and need no further explanation.

The invention claimed is:

1. A surgical insufflation system comprising
a gas insufflator,
a controller operatively coupled to the gas insufflator,
(a) at least one interface for reading patient information, in particular to at least one hospital information system (HIS),
(b) at least one interface for reading procedure information for the respective patient,
(c) at least one memory unit for storing patient data and procedure data received via the interface, (d) at least one memory unit for storing the possible operating parameters of each connected insufflator,
wherein the stored operating parameters of the insufflator include at least the following data: minimum pressure inside the body (pmin), maximum pressure inside the body (pmax), maximum flow in the inlet (Fmax,in), maximum suction power (Fmax,out),
(e) at least one memory unit for storing the allowable operating parameters of an insufflator for different patients,
(f) at least one computing unit for determining the operating parameters for the selected treatment procedure for the respective patient,
(g) at least one interface to the selected insufflator, the interface transmitting patient data, procedure data, and operating parameters to the memory unit of the insufflator,
(h) optionally at least one interface from the insufflator to the hospital information system for transmitting the intraoperative measured data and storing it in the patient record; wherein the controller is configured, in response to receiving the procedure data from the HIS, to pre-adjust one or more operating parameters of the gas insufflator based on the identified procedure class and at least part of the patient-specific data; and
wherein the controller is further configured, prior to activation of the selected procedure, to check whether a consumable assembly required for the identified procedure class is compatible with the selected procedure and, when the check indicates incompatibility, to at least one of (i) inhibit activation of the selected procedure and (ii) output an alert requiring user confirmation to proceed.

2. The medical device for insufflation according to claim 1, wherein the information of the interface (a) is transmitted in encrypted form via LAN, WLAN, Bluetooth, or via an image recognition system for reading a QR code.

3. The medical device for insufflation according to claim 1, wherein the information of the interface (a) includes at least name, patient ID, age, gender, height, weight (BMI).

4. The system of claim 3, wherein the machine-readable identifier comprises at least one of a barcode, a QR code, an RFID tag, or a camera-recognized marking.

5. The medical device for insufflation according to claim 1, wherein the information of the interface (b) is transmitted in encrypted form via LAN, WLAN, Bluetooth.

6. The medical device for insufflation according to claim 1, wherein the information of the interface (b) includes type and body site of the intervention and type of diagnosis/therapy.

7. The medical device for insufflation according to claim 1, wherein operating parameters of available accessories are stored, selected from maximum allowable pressure, humidification option, maximum amount of humidifier.

8. The medical device for insufflation according to claim 1, wherein the memory unit (e) includes maximum internal body pressures for patients
of different ages,
of different heights,
of different BMIs,
depending on the treatment procedure.

9. The system of claim 1, wherein the consumable assembly comprises at least one of: a patient tubing set, a filter, a gas supply line, a gas cylinder or regulator, a smoke evacuation filter, or a trocar seal.

10. The system of claim 1, wherein the controller performs the compatibility check by reading a machine-readable identifier associated with the consumable assembly and comparing the identifier to a compatibility table for the identified procedure class.

11. The system of claim 1, wherein the pre-adjusted operating parameters comprise a set pressure, a maximum pressure limit, a flow-rate setpoint, a ramp-up profile, or a pressure-relief rule parameterized by the procedure class.

12. The system of claim 1, wherein the HIS-provided patient-specific data includes at least one of age, sex, weight, or comorbidities, and the pre-adjustment includes applying procedure-class-specific caps or set-value recommendations based on the patient-specific data.

13. The system of claim 1, wherein detection of an incompatible consumable assembly causes the controller to log the event to an electronic case record associated with the procedure class and to provide a recommended compatible alternative.

14. The system of claim 1, wherein user override of an incompatibility alert requires authentication of surgical staff and records the override to the electronic case record.

15. The system of claim 1, wherein the compatibility check is performed automatically upon association of the consumable assembly to the system and again upon selection of the procedure class.

16. The system of claim 1, wherein the controller updates the compatibility table by downloading, via a secure update channel, device-recognition and materials management data mapping consumables to procedure classes.

\*   \*   \*   \*   \*